United States Patent
Ostaszewski et al.

(10) Patent No.: US 9,018,255 B2
(45) Date of Patent: Apr. 28, 2015

(54) ESTERS OF (ACYLOXYMETHYL)ACRYLAMIDE, A PHARMACEUTICAL COMPOSITION CONTAINING THEM, AND THEIR USE AS INHIBITORS OF THE THIOREDOXIN—THIOREDOXIN REDUCTASE SYSTEM

(75) Inventors: Ryszard Ostaszewski, Komorów (PL); Szymon Klossowski, Podkowa Leśna (PL); Izabela Ziuzia, Bydgoszcz (PL); Angelika Szokalska, Łódź (PL); Marta Swiech, Warsaw (PL); Jakub Golab, Warsaw (PL)

(73) Assignees: Instytut Chemii Organicznej Polskiej Akademii Nauk (PL); Warszawski Uniwersytet Medyczny (PL)

( * ) Notice: Subject to any disclaimer, the term of this patent is extended or adjusted under 35 U.S.C. 154(b) by 0 days.

(21) Appl. No.: 13/879,609

(22) PCT Filed: Oct. 16, 2011

(86) PCT No.: PCT/PL2011/050041
§ 371 (c)(1),
(2), (4) Date: Aug. 15, 2013

(87) PCT Pub. No.: WO2012/050465
PCT Pub. Date: Apr. 19, 2012

(65) Prior Publication Data
US 2013/0317102 A1    Nov. 28, 2013

(30) Foreign Application Priority Data
Oct. 16, 2010   (PL) .......................................... 392651

(51) Int. Cl.
*A01N 37/10* (2006.01)
*A61K 31/235* (2006.01)
*C07C 229/00* (2006.01)
*C07C 235/28* (2006.01)

(52) U.S. Cl.
CPC .................................. *C07C 235/28* (2013.01)

(58) Field of Classification Search
None
See application file for complete search history.

(56) References Cited

PUBLICATIONS

Yagci et al. (Macromol. Mater. Eng., 2006, 291, 336-344).*
Arne Holmgren "Thioredoxin and Glutaredoxin Systems," The Journal of Biological Chemistry (Aug. 25, 1989); 264 (24):13963-13966.
Calabrese et al., "Curcumin and the cellular stress response in free radical-related diseases," Mol. Nutr. Food Res. (2008); 52:1062-1073.
Fang et al., "Thioredoxin reductase is irreversibly modified by curcumin," The Journal of Biological Chemistry (Jul. 1, 2005); 280(26):25284-25290.
Gromer et al., "Human Placenta Thioredoxin Reductase," The Journal of Biological Chemistry (Aug. 7, 1998); 273 (32):20096-20101.
Kirkpatrick et al., "Mechanisms of inhibition of the thioredoxin growth factor system by antitumor 2-imidazolyl disulfides," Biochemical Pharmacology (1998); 55:987-994.
May et al., "Reduction of dehydroascorbate to Ascorbate by the selenoenzyme thioredoxin reductase," The Journal of Biological Chemistry (Sep. 5, 1997); 272(36):22607-22610.
Nordberg et al., "Mammalian thioredoxin reductase is irreversibly inhibited by dinitrohalobenzenes by alkylation of both the redox active selenocysteine andits neighboring cysteine residue," The Journal of Biological Chemistry (May 1, 1998); 273(18):10835-10842.
Sun et al., "Redox regulation of cell signaling by selenocysteine in mammalian thioredoxin reductases," The Journal of Biological Chemistry (Aug. 27, 1999); 274(35):24522-24530.

* cited by examiner

*Primary Examiner* — Dennis Heyer
*Assistant Examiner* — Daniel M Podgorski
(74) *Attorney, Agent, or Firm* — Fox Rothschild LLP; Shahnam Sharareh

(57) ABSTRACT

The subject of the present invention are novel esters of (acyloxymethyl)acrylamide, a pharmaceutical composition containing them and their use in the production of drugs for the prophylaxis or treatment of oncogenic diseases and diseases connected with increased cell proliferation.

8 Claims, 2 Drawing Sheets

Figure 1:
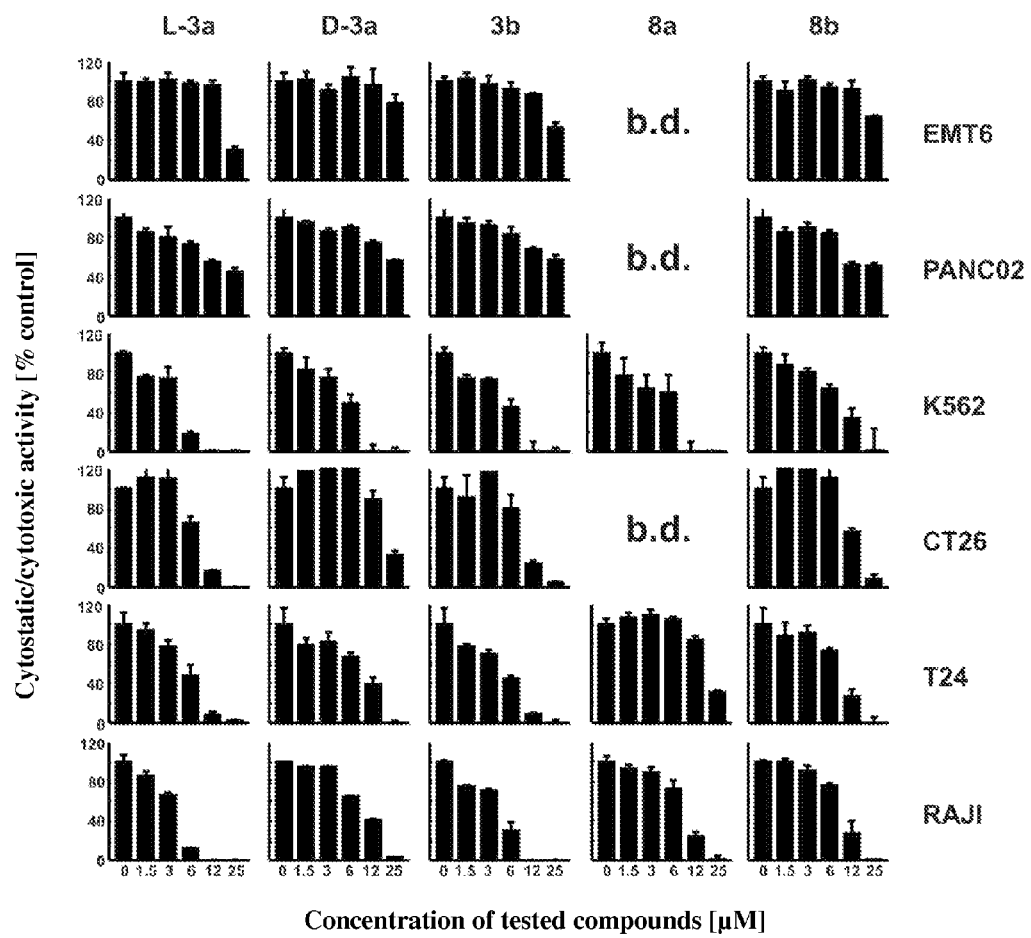

ESTERS OF (ACYLOXYMETHYL)ACRYLAMIDE, A PHARMACEUTICAL COMPOSITION CONTAINING THEM, AND THEIR USE AS INHIBITORS OF THE THIOREDOXIN—THIOREDOXIN REDUCTASE SYSTEM

This application is a U.S. National Phase Application of International Application No. PCT/PL2011/050041 filed Oct. 16, 2011, which claims priority to Polish Application No. 392651 filed Oct. 16, 2010, the disclosures of which are hereby incorporated by reference in their entirety.

The subject of the present invention are novel esters (acyloxymethyl)acrylamide, a pharmaceutical composition containing them and their use in the production of drugs that target the thioredoxin—thioredoxin reductase system. The present invention is for use in medical chemistry, pharmaceuticals and medicine.

The process of carcinogenesis, and also subsequent stages of tumour progression are heavily influenced by enzymes that control the redox state of cells, and among these an enzymatic system composed of two proteins: thioredoxin and thioredoxin reductase (TrxR) seems to play an important role. The basic function of this system is to protect cells against oxidative stress. Both thioredoxin and thioredoxin reductase can reduce a variety of molecules, including reactive oxygen species (ROS). However, it is the ability of the Trx-TrxR system to oxidatively modify large macromolecules, particularly proteins. hat makes this system exceptional in terms of regulating important cellular processes, such as cell survival and proliferation or cell death in apoptotic or non-apoptotic pathways.

During the reduction of particular molecules, thioredoxin is oxidized through the formation of a disulphide bridge between two cysteines in the active centre of the enzyme. Oxidized Trx can no longer function as a reducer, and thus the subsequent step is the regeneration of Trx by thioredoxin reductase. The reductase along with $NADPH_2$ reduces the disulphide bridge, thanks to which thioredoxin regains its activity.

Thioredoxin reductase is an enzyme with a molecular mass of 55 kDa, that occurs in active form as a homodimer (Gromer S et al., *Med. Res. Rev.*, 2004, 24, 1, pp. 40-89). Three isoforms of TrxR exist in mammalian cells: cytoplasmic (TrxR1), mitochondrial (TrxR2) and glutathione TrxR (which exhibits the ability to reduce glutathione). This enzyme has two active sites: the so-called N-terminal active site and the C-terminal active site. The first of them has two cysteine residues at positions Cys59 and Cys64, whereas the C-terminal site contains a cysteine at position Cys497 and, what is interesting, selenocysteine at position Sec498. The presence of selenium instead of a sulphur atom is explained by the decreased tension of S—Se bonds between the neighbouring residues of selenocysteine and cysteine as compared to a bond between two cysteines. In eukaryotic cells, the substrate specificity of TrxR is quite low. In addition to thioredoxin, human reductase may reduce a gamut of other compounds, including the regeneration of the oxidised form of ascorbic acid (vitamin C) (May J. M. et al., *J. Biol. Chem.*, 1997; 272, pp. 22607-22610).

Thioredoxin is a small protein with a mass of about 12 kDa. Its active site is the so-called "thioredoxin motif" containing the sequence: (W)CGPC(K), wherein the amino-acids in brackets may differ between various types of thioredoxins Like in the case of TrxR, during the reduction of target molecules, the cysteine residues (Cys33 and Cys35) in the active site form a disulphide bridge. One of the catalytically active cysteines becomes exposed to the outside of the enzyme, whereas the other is hidden inside. The additional cysteine (Cys73) is used to form the homodimer, characteristic only for mammalian enzymes. Thioredoxin occurs in two isoforms: cytoplasmatic (Trx1) and mitochondrial (Trx-2). Furthermore, there is a number of proteins with thioredoxin activity which perform as yet unexplained functions in various cellular compartments.

The interest in Trx-TrxR system in the context of cancer treatment is based on, amongst others, the increased synthesis of these proteins in tumour cells as compared with normal cells (Berggren, M. et al., *Anticancer Res* 1996, 16, pp. 3459-3466). The increased synthesis of proteins of the Trx-TrxR system is conducive to tumour cells. Thioredoxin participates along with glutaredoxin in the synthesis of deoxynucleotides, being a proton donor for ribonucleotide reductase. In this way, rapidly proliferating cells are supplied with substrates essential to the synthesis of nucleic acids (Holmgren, A., *J. Biol. Chem.* 1989, 264, pp. 13963-13966).

The Trx-TrxR system is also responsible for apoptosis inhibition. This mechanism is based on binding of reduced thioredoxin to ASK1 (apoptosis signal regulating kinase 1). This factor is responsible for the activation of the kinase pathway that initiates apoptosis, and its efficient binding by thioredoxin, which is overexpressed in tumour cells effectively prevents tumour cell death (Ichijo, H. et al., *Science* 1997, 275, pp. 90-94). Furthermore, thioredoxin modulates the activity of the transcription factor NF-κB, which also inhibits apoptosis. Additionally, by increasing the synthesis of HIF-1 (hypoxia inducible factor—1), the Trx-TrxR system positively regulates tumour angiogenesis, increasing tumour growth potential. It was also observed that both the aggressiveness, as well as the drug resistance of tumour cells are correlated with thioredoxin levels.

To summarise, the inhibition of the Trx-TrxR system impairs proliferation of tumour cells, induces their death in apoptotic and non-apoptotic mechanisms, increases the sensitivity of tumour cells to chemotherapeutics, radiotherapy as well as apoptosis inducers, and negatively affects tumour angiogenesis.

In medicine, there is a need to develop selective Trx-TrxR system inhibitors, which are potentially very effective anti-tumour drugs, which may be used in monotherapy as well as in combined therapy with other, already registered, forms of cancer treatment.

In recent years, a group of chemotherapeutics has been synthesized that inhibit the Trx-TrxR system. The target of the inhibitors is both thioredoxin itself as well as thioredoxin reductase. In designing inhibitors, the initial consideration has to be made to the active sites of both enzymes. Most of the known inhibitors bind (reversibly or not) the two cysteines of the active site (selenocysteine in human TrxR).

The Table below summarizes the known inhibitors of the Trx-TrxR system.

| | | |
|---|---|---|
| Cisplatin (CDDP) | 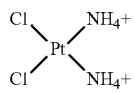 1 | Testicular and prostate cancer, small lung tumors |
| CDDP-Nitrofuran | 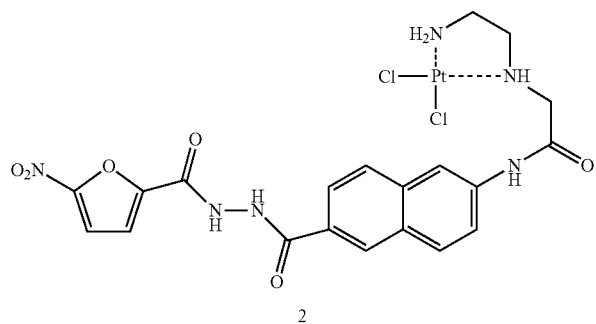 2 | |
| PX-12 | 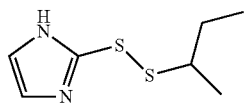 4 | Phase II clinical trials for pancreatic cancer treatment |
| Alkylating factors | 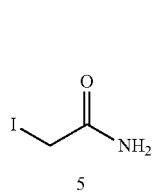 5 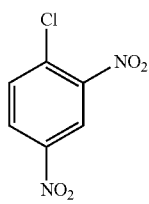 6 | Alkylate cysteine and selenocysteine residues |
| Curcumin | 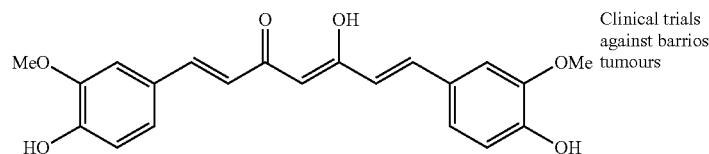 7 | Clinical trials against barrios tumours |
| Palmarumicin | 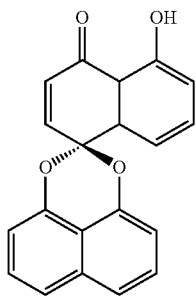 8 | Breast cancer, lung tumours |

The Table below summarizes the known inhibitors of the Trx-TrxR system.

Auranofin

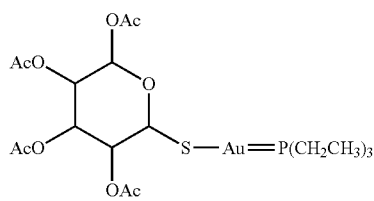

9

Ovarian cancer

One of the oldest inhibitors of thioredoxin, long used in tumour therapy, is cisplatin (1), as well as its newer analogues (2). The mechanism by which platinum compounds act in tumour cells is based on the direct disruption of DNA, which results in the formation of durable adducts. It turns out, however, that being a good electrophile, a platinum compound is an effective inhibitor of thioredoxin reductase. Strong enough in fact that it may even affect the enzyme in stoichiometric quantities (Sasada, T. et al., *Free Radic. Biol. Med.* 1999, 27, pp. 504-514).

Another compound which selectively inhibits thioredox inactivity is 1-methylpropyl-2-imidazole disulphide, PX-12 (4). It was discovered during the design process of a thioredoxin reductase inhibitor, and has already been evaluated in phase II clinical trials for the treatment of advanced pancreatic cancer. An interesting fact in terms of medicinal chemistry is that the methyl group in the alkyl chain is necessary for inhibitory activity. Compounds of similar structure, but lacking this group were not thioredoxin inhibitors but substrates. PX-12 may reversibly form disulphides in the active sites of both TrxR and Trx, which leads to their oxidation. However, thus oxidized enzymes may be regenerated and the inhibition results from the binding of Cys73. First, this blocks the formation of the Trx active dimer, and secondly, thioredoxin bound at this position will no longer be a substrate for thioredoxin reductase, and thus cannot be regenerated (Kirkpatrick, D. L. et al., *Biochem. Pharmacol.* 1998, 55, pp. 987-994). An additional activity of PX-12 observed in vivo is the inhibition of VEGF (vascular endothelial growth factor) synthesis. The increased synthesis of thioredoxin in tumour cells often lads to increased VEGF expression, which in turn accelerates angiogenesis inside the tumour. If the VEGF concentration is decreased, vasogenesis of capillaries in the tumour also drops off, which additionally slows tumour growth.

Curcumin (7), a compound of natural origin extracted from *Curcuma longa*, is an interesting compound primarily because of its broad spectrum of activity. Aside from use as a condiment (component of curry), in Asian cultures curcumin was used to treat various illnesses, from anorexia, through coughing, liver diseases to sinus infections (Calabrese, V. et al., *Mol. Nutr. Food Res.* 2008, 52, pp. 1062-1073). Looking at the chemical structure of curcumin one easily notices electrophyllic centres in the form of Michael acceptors. They may interact with nucleophylic residues of selenocysteine and cysteine in the active centres of the Trx-TrxR system. It turns out that curcumin actually strongly inhibits thioredox reductase activity, both in isolated enzyme activity assays and in Hela cell extracts (Fang, J., Lu, J., Holmgren, A., *J. Biol. Chem.* 2005, 280. pp. 25284-25290). Curcumin, however, is not a selective inhibitor of this system because it affects many kinases, cyclins or cyclooxygenase.

Because the active centre of thioredoxin with cysteine or selenocysteine residues it may be viewed as a nucleophylic centre, it is possible to suggest that alkylating agents will covalently and irreversibly inhibit the activity of the enzyme. Two known sulphur alkylating agents (Sun, Q. et al., *J. Biol. Chem.* 1999, 274, pp. 24522-24530): iodoacetamide (5) or iodoacetic acid were examined in terms of their antitumour activity, but due to their low selectivity they are of limited use as chemotherapeutics. Both, however, demonstrate strong thioredoxin reductase activity inhibition. 1-chloro-2,4-dinitrobenzene is a small compound, which alkylates both selenocysteine residues and neighbouring cysteine residues (Nordberg, J. et al., *J. Biol. Chem.* 1998, 273, pp. 10835-10842). Such an alkylated TrxR activates mitochondrial caspases, which elicits a cytotoxic effect, against human lung cancer amongst others.

Gold compounds were initially used in the treatment of rheumatoid disease, but due to their strong cytotoxic activity against tumour cells, an increasing number of chemotherapeutics based on gold (I) or gold (III) compounds are becoming available. The mechanism of activity of these compounds is still not entirely clear. It is postulated that this is similar to platin, or one based on direct DNA damage. However, because gold has a high affinity for thiol groups it is possible that thioredoxin may be a cellular target of these therapeutics. An example of such a compound is auranofin (9), known for its anti-rheumatoid activity. It inhibits thioredoxin reductase in nanomolar concentrations, whereas it inhibits glutathione reductase at micromolar levels (Gromer, S. et al., K., *J. Biol. Chem.* 1998, 273, pp. 20096-20101). Glutathione reductase lacks a C-terminal active site with selenocysteine. It is thus possible that this site is the target of auranofin activity. The cytotoxicity of auranofin was evaluated against tumour cells which have become resistant to cisplatin (Marzano, C. et al., *Free Radic. Biol. Med.* 2007, 42, pp. 872-881) and clear inhibition of TrxR was observed (with a parallel lack of glutathione reductase activity inhibition) and a high cytotoxicity, which has opened novel possibilities in the treatment of tumours resistant to cisplatin therapy. It is interesting that TrxR activity is much higher in cells resistant to cisplatin. This confirms the important role of increased thioredoxin reductase and thioredoxin synthesis in resistance to chemotherapeutics.

As is evident from the above descriptions of known inhibitors of the Trx-TrxR system, most of them react directly with thiol or selenium residues in both enzymes. The interactions are strong covalent bonds or permanent complexes with metals. However, the mechanisms of activity of many of them are still unclear. Due o the fact that the inhibitors known to date are very active molecules, a number of them may exhibit undesirable effects based on low selectivity against cysteine residues in other enzymes.

The goal of the present invention is to indicate novel inhibitors of the thioredoxin—thioredoxin reductase system, both effective and more selective than currently available. The factor that differentiates the Trx-TrxR system in this respect is the selenocysteine residue, which is a stronger nucleophile than cysteine, which may be crucial to inhibitor selectivity.

Unexpectedly, this goal was attained by producing novel aryl esters of (2-hydroxymethyl)acrylamide and carboxylic acids. Compounds according to the present invention have turned out to be effective inhibitors of thioredoxin (Trx). These compounds simultaneously exhibit strong antitumour properties.

The subject of the present invention is thus compounds defined by the general formula (1):

$$\underset{R3\diagdown O}{\phantom{X}}\diagdown \underset{O}{\phantom{X}} \diagdown \underset{}{\overset{O}{\underset{}{\|}}} \diagdown \underset{H}{N} \diagdown \underset{R2}{\overset{R1}{\phantom{X}}} \quad (1)$$

where:
R1 denotes a linear or branched C1-C8 alkyl group, substituted or not substituted with a phenyl or benzyl group,
R2 denotes hydrogen, an alkyl 2-formamidoacetate group, wherein the alkyl group possesses a straight or branched chain from C1 to C8, and
R3 denotes a carboxylic acid acyl group selected from 2,6-dichlorobenzoic or 2,6-di(trifluoromethyl)benzoic acid groups;
or its pharmaceutically permissible salt.

Preferably, these compounds are selected from a group encompassing compounds defined by the general formula:

N—(R1,R2-methyl)-2-[(acyloxy]methacrylamide where:
R1 denotes a linear or branched C1-C8 alkyl group, substituted or not substituted phenyl group, benzyl,
R2 denotes a hydrogen atom, or CONHCH2COOX group, where X is a linear or branched C1-C6 aliphatic substituent,
R3 denotes a phenyl substituent or a complex phenyl substituent possessing at positions 2,6 two identical or different halide (Cl, Br, I) or trifluoromethyl substituents.

In particular the subject of the present invention are compounds selected from a group encompassing:
(R)-2-((1-((2-ethoxy-2-oxoethyl)amino)-4-methyl-1-oxopentan-2-yl)carbamoyl)allyl 2,6-bis(trifluoromethyl)benzoate;
(S)-2-((1-((2-ethoxy-2-oxoethyl)amino)-4-methyl-1-oxopentan-2-yl)carbamoyl)allyl 2,6-bis(trifluoromethyl)benzoate;
2-((1-((2-ethoxy-2-oxoethyl)amino)-4-methyl-1-oxopentan-2-yl)carbamoyl)allyl 2,6-bis(trifluoromethyl)benzoate;
2-((1-((2-ethoxy-2-oxoethyl)amino)-4-methyl-1-oxopentan-2-yl)carbamoyl)allyl 2,6-dichlorobenzoate;
2-(benzylcarbamoyl)allyl 2,6-bis(trifluoromethyl)benzoate;
2-(benzylcarbamoyl)allyl 2,6-dichlorobenzoate.

The next subject of the present invention is the use of a compound with the general formula (1) or its pharmaceutically permissible salts as drugs.

The above use is preferably characterised in that the drug is meant for the prophylaxis or treatment of oncogenic diseases, diseases connected with increased cell proliferation, preferably acute and chronic transplant rejection, allergic and autoimmune diseases, lymphoid proliferative syndromes, myelodisplastic and myeloproliferative syndromes and pre-oncogenic states.

The subject of the present invention is a pharmaceutical composition characterised in that it contains as its active ingredient a compound with the general formula (1) or its pharmaceutically permissible salt.

A pharmaceutical composition according to the present invention is preferably meant for the prophylaxis or treatment of oncogenic diseases, diseases connected with increased cell proliferation, preferably acute and chronic transplant rejection, allergic and autoimmune diseases, lymphoid proliferative syndromes, myelodisplastic and myeloproliferative syndromes and pre-oncogenic states.

The next subject of the present invention is a method of producing a compound with the general formula (1), in which the amide bond formation is performed by coupling a carboxylic acid with the amine component in an organic solvent, in the presence of a coupling reagent.

Figure 2:
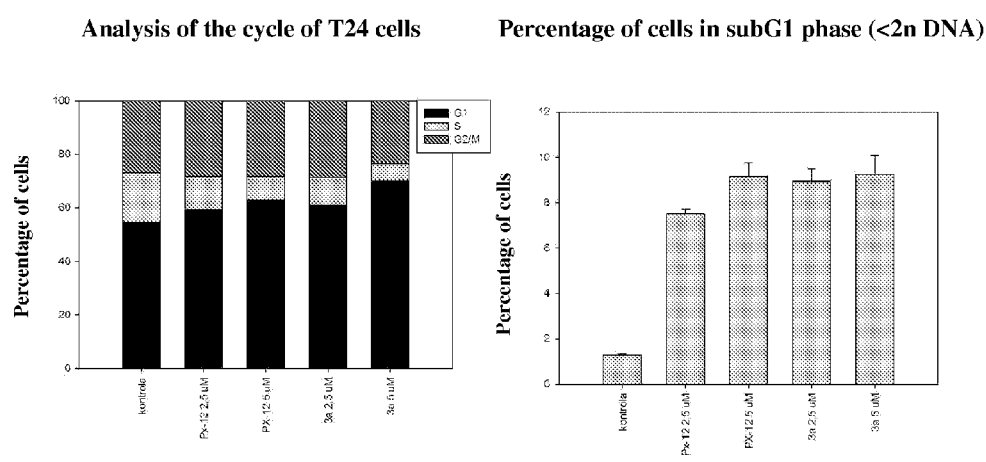

The subject the present invention is illustrated in example embodiments in the figure, where FIG. 1 shows compilation of experimental results determining the cytostatic/cytotoxic activity of the evaluated compounds (in columns) against a number of tumour cells (description of the POM line on the right side). The cytostatic/cytotoxic activity against adherent cells, from solid tumours cells (EMT6, PAN02, CT26 and T24) was evaluated using the crystalline violet test, whereas against suspension-grown cells of the MTT line. b.d.=no data.

whereas FIG. 2 shows an analysis of the cycle of T24 cells following incubation with thioredoxin inhibitors.

According to the present invention, experiments showed that esters of (acyloxymethyl)acrylamide have considerably more preferable pharmacological properties than 1-methyl-propyl-2-imidazole disulphide, referred to in literature as PX-12. They inhibit thioredoxin activity more effectively than PX-12, they are more selective (in larger concentrations they inhibit thioredoxin reductase and, in contrast to PX-12, do not inhibit glutathione reductase), exhibit cytostatic/cytotoxic activity against human and murine tumour cells originating from both solid tumours (breast, kidney, colon and pancreatic cancer), as well as of the hematopoietic system (leukaemias and lymphomas).

Compounds according to the present invention, denoted herein as: 3a, L-3a, D-3a, 3b, 8a and 8b inhibit thioredox inactivity at concentrations smaller than compound PX-12, the reference inhibitor of the enzyme, whose antitumour activity is currently undergoing clinical testing.

Compounds 3a, 8a and 8b are also more selective than PX-12. For example, compound 3a inhibits the activity of activity recombinant thioredoxin three times stronger and inhibits the activity of recombinant thioredoxin reductase about three times less in comparison to the reference compound PX-12. Furthermore, the greater selectivity of compound 3a was also demonstrated in tests relating to glutathione reductase. The cytostatic/cytotoxic activity of 3a and PX-12 is comparable against the examined lines of human and murine of tumour cells.

Likewise, compound L-3a, D-3a, 3b, 8a and 8b exhibit strong cytostatic/cytotoxic activity against the panel of human and murine lines of tumour cells. The indicated inhibitory effect of the tested compounds on cell division makes it possible to use them both in the treatment of neoplastic diseases, as well as other diseases, where excessive cell proliferation occurs.

The subject of the present invention is also a pharmaceutical composition meant for the treatment of neoplastic diseases, containing as its active ingredient esters of (acyloxymethyl)acrylamide in an amount sufficient to elicit a cytotoxic effect, along with at least one inert, pharmaceutically permissible carrier, diluent or ancillary substance as well as a pharmaceutical composition designed for the treatment of neoplastic diseases, containing as its active ingredient, racemic or enantiomer-enriched 2-((1-((2-ethoxy-2-oxoethyl)amino)-4-methyl-1-oxopentan-2-yl)carbamoyl)allyl 2,6-bis(trifluoromethyl)benzoate, 2-((1-((2-ethoxy-2-oxoethyl)amino)-4-methyl-1-oxopentan-2-yl)carbamoyl)allyl 2,6-dichlorobenzoate, 2-(benzylcarbamoyl)allyl 2,6-bis(trifluoromethyl)benzoate, 2-(benzylcarbamoyl)allyl 2,6-dichlorobenzoate in an amount sufficient to elicit cytostatic/cytotoxic effects, along with at least one inert, pharmaceutically permissible carrier, diluent or ancillary substance.

The subject of the present invention, esters of (acyloxymethyl)acrylamide, may be used in therapy in the form of pharmaceutical compositions designed for oral and parenteral administration. Such compositions may be manufactured using methods of producing drug forms known from prior art.

Compounds according to the present invention may thus be manufactured and administered in diverse forms for parenteral and oral administration. Therefore, a compound according to the present invention, may be administered via intravenous, intramuscular, dermal, subcutaneous, and intraperitoneal injections.

For parenteral administration liquid dosage forms are manufactured using each of the compounds according to the present invention, that is 2-((1-((2-ethoxy-2-oxoethyl)amino)-4-methyl-1-oxopentan-2-yl)carbamoyl)allyl 2,6-bis(trifluoromethyl)benzoate, 2-((1-((2-ethoxy-2-oxoethyl)amino)-4-methyl-1-oxopentan-2-yl)carbamoyl)allyl 2,6-dichlorobenzoate, 2-(benzylcarbamoyl)allyl 2,6-bis(trifluoromethyl)benzoate, 2-(benzylcarbamoyl)allyl 2,6-dichlorobenzoate and an inert vehicle, wherein preferably water is used. The aforementioned compounds, depending on the type of pharmaceutically compatible carrier may be suspended, or dissolved in the vehicle. When manufacturing a solution, the active compound may be dissolved in the injectible solution and sterilised by filtration. The resulting sterile solution is transferred into vials or ampoules and sealed.

The preparation, following aliquotting into vials, may be frozen or the solvent may be removed under vacuum. Next, the lyophilised powder is sealed in the vial, and alotted with a vial of injectible water for the preparation of the injectible drug. It is obvious to a specialist that the aforementioned dosage forms may contain as their active ingredient both the novel compound as well as a pharmaceutically permissible salt of each of the compounds according to the present invention.

Compounds according to the present invention, esters of (acyloxymethyl)acrylamide are useful in the treatment of oncogenic diseases. Due to strong cytostatic activity (cell cycle arrest in phase G1, decrease of the percentage of cells undergoing DNA synthesis). Their desirable properties also make them useful for the treatment of diseases, whose pathogenesis involves increased cell proliferation, such as acute and chronic transplant rejection, allergic and autoimmune diseases, lymphoid proliferative syndromes, myelodysplastic and myeloproliferative syndromes and other pre-oncogenic states.

The present invention us illustrated by the following example embodiments:

1. A method of obtaining a compound with the general formula

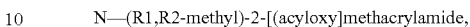

N—(R1,R2-methyl)-2-[(acyloxy]methacrylamide, defining novel esters of acyloxymethacrylamide defined by formula 1, in which R1 denotes a linear or branched C1-C8 alkyl group, substituted or non-substituted phenyl group, or benzyl, R2 denotes a hydrogen atom, or CONHCH2COOX group, where X is a linear or branched C1-C6 aliphatic substituent, R3 denotes a phenyl substituent or a complex phenyl substituent possessing at positions 2,6 two identical or different halide substituents (Cl, Br, I) or trifluoromethyl.

1.1. Racemic peptidomimetics R1=iBu, R2=H, R3=CONH$_2$CH$_2$COOEt

Scheme 1:

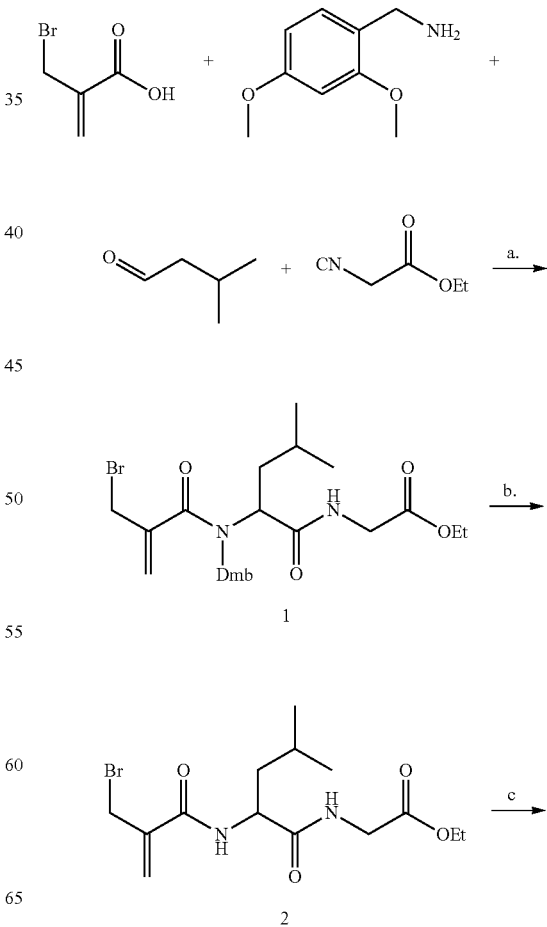

-continued

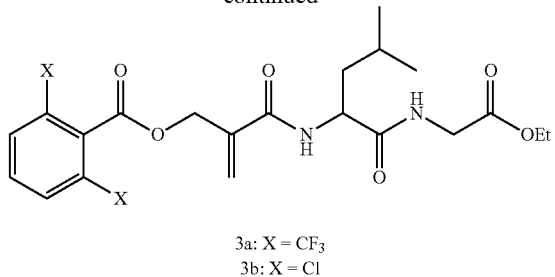

3a: X = CF$_3$
3b: X = Cl a) methanol, RT, 16 h, 46%
b) TFA, CH$_2$Cl$_2$, 30 min, RT 70%
c) 4, acetone, boiling temperature, 59-87%

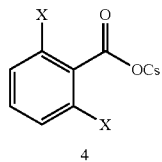

4

Compound 1: Ethyl 2-(2-(2-(bromomethyl)-N-(2,4-dimethoxybenzyl)acrylamido)-4-methylpentaneamido)acetate A solution of isovaleric aldehyde (96 μl, 0.88 mmol) in methanol (1 ml) was supplemented with 2,4-dimethoxybenzylamine (133 μl, 0.88 mmol) and mixed for 30 minutes. Next, this was supplemented with bromomethylmethacrylic acid (146 mg, 0.88 mmol) and mixed for another 30 minutes. The mixture was cooled to a temperature of 0° C. and was supplemented with ethyl isocyanoacetate (100 μl, 0.88 mmol), and then mixed for 20 hours at room temperature. The solvent was evaporated off and the remainder purified using column chromatography in a hexane: ethyl acetate system (silica gel, R$_f$=0.33, 5:5, v:v).

This yielded 207 mg of transparent oil (46%).

$^1$H NMR (200 MHz, CDCl$_3$): δ 0.84-0.89 (m, 6H), 1.21-1.28 (m, 5H), 1.54-1.67 (m, 1H) 1.91-1.98 (m, 1H), 3.77 (s, 3H), 3.77 (s, 3H), 3.85 (d, J=5.2 Hz), 4.04-4.23 (m, 4H), 4.55-4.70 (m, 2H), 5.43 (s, 1H), 5.54 (s, 1H), 6.39-6.43 (m, 2H), 7.43 (d, J=9.2 Hz, 1H) $^{13}$C NMR (50 MHz, CDCl$_3$): δ 14.5, 22.8, 22.9, 25.5, 33.4, 37.6, 41.7, 55.6, 55.6, 59.1, 61.6, 98.7, 104.3, 119.3, 130.3., 140.4, 169.8. HR-MS (ESI, [M+Na$^+$]) calculated for C$_{23}$H$_{33}$BrN$_2$O$_6$Na: 535, 1414. found: 535.1402;

Compound 2: Ethyl 2-(2-(2-(bromomethyl)acrylamido)-4-methylpentaneamido)acetate

Compound 1 (117 mg, 0.23 mmol) was dissolved in methylene chloride (2 ml). Next, this was supplemented with trifluoroacetic acid (475 μl) at room temperature. The mixture was left for 1 hour while observing the colour change from clear to dark violet. The flask contents were transferred into a separator, and this was supplemented with methylene chloride (4 ml) and a saturated solution of sodium carbonate was added until the disappearance of the violet colour. The aqueous phase was extracted with methylene chloride (3×8 ml), and then the combined organic phases were dried with brine and the solvent was evaporated off. The remainder was purified using column chromatography in a hexane: ethyl acetate system (silica gel, R$_f$=0.25, 6:4, v:v).

This yielded 58 mg of product (70%).

$^1$H NMR (200 MHz, CDCl$_3$): δ 0.87-0.94 (m, 6H), 1.22-1.29 (m, 5H), 1.38-1.70 (m, 4H), 3.96 (d, J=5.2 Hz, 1H), 4.01 (d, J=5.8 Hz, 1H), 4.10-4.23 (m, 5H), 4.60-4.78 (m, 1H), 5.69 (s, 1H), 5.85 (s, 1H), 6.90 (d, J=8.0 Hz, 1H), 7.14 (m, 1H). $^{13}$C NMR (50 MHz, CDCl$_3$): δ 14.5, 22.4, 23.3, 25.1, 30.7, 41.4, 41.7, 52.1, 61.8, 123.0. 141.3, 166.4, 170.0. 172.6; HR-MS (ESI, [M+Na$^+$]) calculated for C$_{14}$H$_{23}$BrN$_2$O$_4$Na: 385.0733. found: 385.0740.

General Method No. 1 of Producing Racemic Compound 3a-b:

Compound 2 0.1 mmol, was dissolved in acetone and was then supplemented with the cesium salt of a carboxylic acid 0.30 mmol). The reaction was performed for 30 min at boiling temperature. The solvent was evaporated off, the remainder was dissolved in ethyl acetate and water. The aqueous phase was extracted with ethyl acetate, and then the combined organic phases were rinsed with a saturated solution of sodium bicarbonate, and then with brine. This was dried with anhydrous magnesium sulphate. The solvent was evaporated off and the remainder purified on a chromatography column in a hexane: ethyl acetate system (silica gel).

Compound rac-3a: 2-((1-((2-ethoxy-2-oxoethyl)amino)-4-methyl-1-oxopentan-2-yl)carbamoyl)allyl 2,6-bis(trifluoromethyl)benzoate Produced using general method II. White powder, t$_t$=114-115° C., yield 87%. R$_f$=0.61 (5:5, v:v). $^1$H NMR (200 MHz, CDCl$_3$): δ 0.85-0.91 (m, 6H), 1.21-1.28 (m, 4H), 1.51-1.70 (m, 4H), 3.46 (d, J=5.2 Hz, 1H), 4.08 (d, J=5.8 Hz, 1H), 4.10-4.19 (m, 3H), 4.60-4.78 (m, 1H), 5.10 (s, 2H), 5.79 (s, 1H), 6.02 (s, 1H) 6.74 (d, J=8.2 Hz, 1H), 6.98-7.03 (m, 1H), 7.72 (d, J=7.8 Hz, 1H), 7.91 (d, J=7.8 Hz, 2H). $^{13}$C NMR (50 MHz, CDCl$_3$): d 14.4, 22.4, 23.0. 25.0. 30.7, 41.2, 41.6, 51.9, 61.8, 65.6, 120.0. 124.3, 125.8, 129.0. 129.7, 130.2, 130.7 137.9, 166.4, 169.9, 172.6; Elemental analysis calculated for C$_{23}$H$_{26}$F$_6$N$_2$O$_6$: C, 51.11; H, 4.85; N, 5.18. found: C, 51.00; H, 5.07; N, 4.86;

Compound rac-3b: 2-((1-((2-ethoxy-2-oxoethyl)amino)-4-methyl-1-oxopentan-2-yl)carbamoyl)allyl 2,6-dichlorobenzoate Produced using general method II. White powder, t$_t$=120-121° C., yield 59%. R$_f$=0.34 (5:5, v:v). $^1$H NMR (200 Mhz, CDCl$_3$) δ 0.83 (d, J=6 HZ, 6H), 1.16-1.30 (m, 3H), 1.47-1.69 (m, 4H), 3.91 (d, J=5.2 Hz, 1H), 3.95 (d, J=5.6 Hz, 1H), 4.12 (q, J=7.2 Hz, 2H), 4.51-4.60 (m, 1H), 5.07 (d, J=4.2 Hz, 2H), 5.78 (s, 1H), 6.00 (s, 1H), 6.56 (d, J=8.2 Hz, 1H), 6.77 (bs, 1H), 7.20-7.25 (m, 3H) $^{13}$C NMR (50 MHz, CDCl$_3$) δ 14.5, 22.4, 23.2, 25.1, 41.2, 41.7, 51.9, 61.9, 65.1, 124.6, 128.2, 131.4, 132.2, 138.1, 166.4, 169.8, 172.28; HR-MS (ESI, [M+Na$^+$]) calculated for C$_{21}$H$_{26}$N$_2$O$_6$NaCl$_2$: 495.10601.0733,found: 495.10812.

1.2. Chiral, non-racemic peptidomimetics 3a-b

Scheme 2:

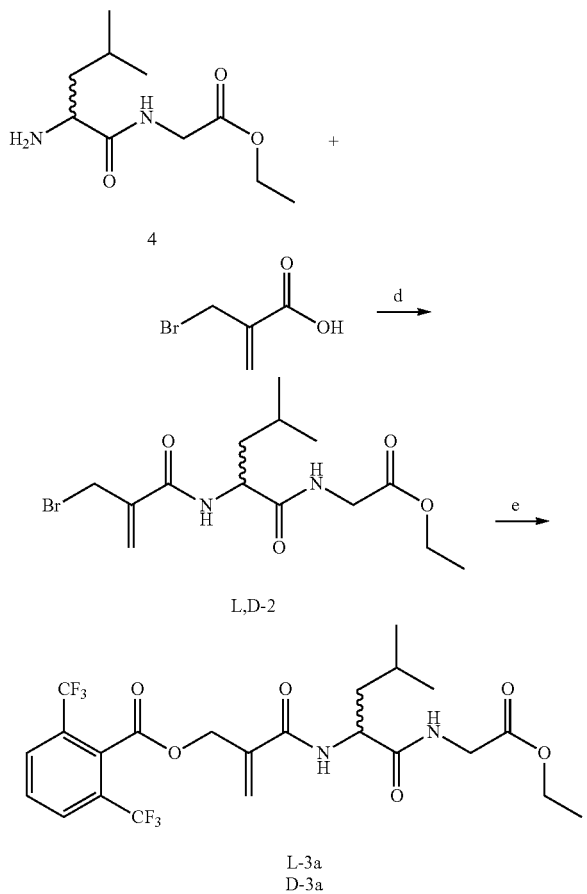

SOCl$_2$, CH$_2$Cl$_2$, 24 h, RT 5-6%;
e) 4, acetone, boiling temperature, 2 h, 33-67%

Compound D-3a: (R)-2-((1-((2-ethoxy-2-oxoethyl) amino)-4-methyl-1-oxopentan-2-yl)carbamoyl)allyl 2,6-bis(trifluoromethyl)benzoate Bromomethacrylic acid (150 mg, 0.9 mmol) was supplemented with freshly distilled thionyl chloride (162 µl, 2.2 mmol). The mixture was mixed at boiling temperature for 2 hours. Excess thionyl chloride was evaporated off under reduced pressure. This was supplemented with methylene chloride (2 ml). The acid chloride solution was cooled to a temperature of 0° C., and supplemented with DMAP (45 mg, 0.4 mmol) and a solution of NH$_2$-D-Leu-Gly-OEt (80 mg, 0.4 mmol) in methylene chloride (2 ml), and mixed 1.5 hours at a temperatutre of 0° C., and then for 2 hours at room temperature. The solvent was evaporated off and the remainder was purified on a chromatography column (R$_f$=0.45 hexane: ethyl acetate 6:4 v/v, as for rac-2). This yielded 12 mg of transparent oil (efficiency 6%).

The thusly prepared compound D-2 (R)-ethyl-2-(2-(2-(bromomethyl)acrylamido)-4-methylpentaneamido)acetate, was dissolved in acetone (5 ml), and supplemented with the cesium salt of bis-(trifluoromethyl)benzoic acid (39 mg, 0.1 mmol). This was mixed at room temperature for 16 hours, and then at boiling temperature for 4 hours. The precipitate was filtered out, the solvent was evaporated off, and the remainder was purified on a chromatography column (R$_f$=0.61 hexane: ethyl acetate 5:5 v/v, as for rac-3a), yielding 12 mg of transparent oil with an efficiency of 67%. HR-MS (ESI, [M+Na$^+$]) calculated for C$_{23}$H$_{26}$F$_6$N$_2$O$_6$Na: 563.1587. found: 563.1592; [α]$_D$=+20° (c=1.2, CHCl$_3$)

Compound L-3a: (S)-2-((1-((2-ethoxy-2-oxoethyl) amino)-4-methyl-1-oxopentan-2-yl)carbamoilo)allyl 2,6-bis(trifluoromethyl)benzoate Bromomethacrylic acid (84 mg, 0.5 mmol) was supplemented with freshly distilled thionyl chloride (111 µl, 1.5 mmol). The mixture was mixed at reflux temperature for 2 hours. Excess thionyl chloride was evaporated off under reduced pressure. This was supplemented with methylene chloride (2 ml). The acid chloride solution was cooled to a temperature of 0° C. and supplemented with DMAP (62 mg, 0.5 mmol) and a solution of NH$_2$-L-Leu-Gly-OEt (110 mg, 0.5 mmol) in methylene chloride (2 ml). The mixture was mixed for 1.5 hours at a temperature of 0° C., and then for 2 hours at room temperature. The solvent was evaporated off and the remainder was purified on a chromatography column. (R$_f$=0.46 hexane:ethyl acetate 6:4, v/v, as for rac-2). This yielded 18 mg of transparent oil (yield 5%).

The thusly prepared compound L-2 (S)-ethyl 2-(2-(2-(bromomethyl)acrylamido)-4-methylpentaneamido)acetate (16 mg, 0.04 mmol) was dissolved in acetone (1 ml) and supplemented with the cesium salt of 2,6-bis-(trifluoromethyl)-benzoic acid (36 mg, 0.09 mmol). The suspension was brought to boiling temperature and was mixed until the substrate disappeared (TLC, 2 hours). The mixture was sieved through a celite to remove excess cesium salt and cesium bromide. The solvent was evaporated off and the remainder was dissolved in ethyl acetate 10 ml. This was rinsed in the following sequence: with water (5 ml), with a saturated solution of sodium carbonate (5 ml) and with brine. The organic phase was dried with anhydrous magnesium sulphate, filtered and evaporated off. The resulting oil was filtered through a silica gel, eluting in a hexane: ethyl acetate system. This yielded 8 mg of product (efficiency 33%). HR-MS (ESI, [M+Na$^+$]) calculated for C$_{23}$H$_{26}$F$_6$N$_2$O$_6$Na: 563.1587. found: 563.1582 [α]$_D$=−23° (c=0.8, CHCl$_3$). the $^1$H NMR spectrum of both enantiomers is fully identical to the spectrum of compound rac-3a.

1.3. Amides R1=R2=H, R3=Ph

Scheme 3:

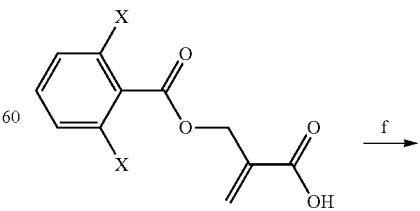

7a: CF$_3$
7b: Cl

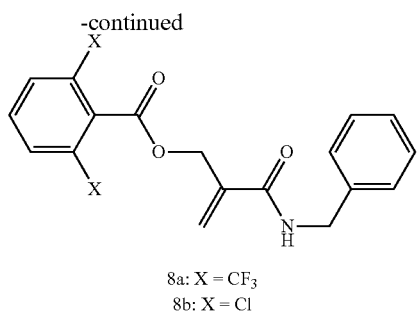

8a: X = CF$_3$
8b: X = Cl f) iBuOCOCl, DMAP, DIPEA, BnNH$_2$

A solution of acid 7 (0.7 mmol) in THF (5 ml) was supplemented with isobutyl chloroformate (0.7 mmol) at a temperature of −10° C. and mixed for 30 min. Next, this was supplemented with benzylamine (0.7 mmol). The mixture was mixed for 2 hours at a temperature of −10° C. and for 1 hour at room temperature. The solvent was evaporated, and the remainder was dissolved in ethyl acetate (20 ml) and rinsed in a sequence of a saturated solution of sodium bicarbonate (10 ml), citric acid (10%, 10 ml) and with brine (10 ml). The remainder was purified on a chromatography column (silica gel, hexane: ethyl acetate).

Compound 8a: 2-(benzylcarbamoyl)allyl 2,6-bis(trifluoromethyl)benzoate $^1$H NMR (CDCl$_3$, 200 MHz) δ 4.50 (d, J=5.8 Hz, 2H,), 5.13 (s, 2H), 6.03 (s, 1H), 6.37 (bs, 1H), 7.28 (s, 5H), 7.71 (t, J=7.8 Hz, 1H), 7.91 (d, J=7.8 Hz, 2H); $^{13}$C NMR (CDCl$_3$, 50 MHz) δ 44.1, 66.0. 124.5, 125.8, 127.9, 128.1, 129.0. 130.1, 130.2, 130.7, 138.1, 138.4, 166.1 Elemental analysis: calculated for: C$_{20}$H$_{21}$NO$_3$: C, 55.69; H, 3.51; N, 3.25. found: C, 55.61; H, 3.38; N, 3.21;

Compound 8b: 2-(benzylcarbamoyl)allyl 2,6-dichlorobenzoate $^1$H NMR (CDCl$_3$, 200 MHz) δ 4.45 (d, J=6 Hz, 2H), 5.09 (s, 1H), 5.75 (s, 1H) 6.0 (s, 1H), 6.35 (bs, 1H), 7.18-7.24 (m, 8H). $^{13}$C NMR (CDCl$_3$, 50 MHz): δ 44.2, 65.5, 124.7, 127.9, 128.2, 129.0. 131.5, 132.2, 138.1, 138.4, 164.5, 166.0; Elemental analysis calculated for C$_{18}$H$_{15}$Cl$_2$NO$_3$. 1H$_2$O: C, 56.56; H, 4.48; N, 3.66. found: C, 56.89; H, 4.36; N, 3.28

2. In vitro Assay Results 2.1. Evaluation of the Thioredoxin—Thioredoxin Reductase System and Glutathione Reductase Activity Using Recombinant Enzymes 2.1.1. Determination of Thioredoxin Activity The method of determining thioredoxin activity is based on the reduction of insulin by thioredoxin. Thioredoxin is reconstituted is by thioredoxin reductase, with NADPH. The resulting free thiol —SH groups react with 5,5'-dithiobis-2-nitrobenzoic acid (DTNB). The termination of the reaction results in the formation of a red colour. The intensity of colouration is determined spectrophotometrically at 412 nm and this corresponds to the number of reduced sulfahydryl groups. The reaction was performed at 37° C. over 30 min. in a buffer containing 50 mM Tris-HCl and 20 mM EDTA at a pH of 7.6. The substrate concentrations used were: 0.25 μM human recombinant thioredoxin and 0.325 μM rat recombinant thioredoxin reductase (IMCO Corporation Ltd AB, Sweden) and 316 μM of insulin, 0.8 μM NADPH, 8 mM DTNB (Sigma Aldrich).

Table 1 summarises the results of inhibiting thioredoxin in the above system. Unexpectedly, all of the examined compounds turned out to inhibit thioredoxin enzymatic activity at lower concentrations than the known inhibitor PX-12. The highest activity was demonstrated by compounds 3a, L-3a, D-3a and 3b, for which the IC$_{50}$ was about 5 times lower than for PX-12.

TABLE 1

| Examined compound | IC$_{50}$ [μM] |
|---|---|
| PX-12 | 15.4 |
| 3a | 3.2 |
| L-3a | 2.8 |
| D-3a | 3.5 |
| 3b | 2.9 |
| 8a | 8.6 |
| 8b | 5.9 |

2.1.2. Evaluation of Thioredoxin Reductase Activity Using a Recombinant Enzyme

Reactions in which the activity of recombinant rat thioredoxin reductase was determined made use of a chromogenic reaction with 5,5'-dithiobis-2-nitrobenzoic acid. The NADP formed as a result of thioredoxin reductase activity reacts with DTNB yielding a yellow hue in solution, whose intensity is determined spectrophotometrically at 412 nm after 5 and 15 min. of incubation at room temperature. The reaction made use of reagents according to the Thioredoxin Reductase Assay Kit (Sigma) and rat recombinant thioredoxin reductase at a concentration of 0.165 μM. Table 2 shows IC$_{50}$ values of the inhibition of thioredoxin reductase activity by PX-12, 3a, 8a and 8b. The most highly active of the examined compounds was PX-12, which inhibited thioredoxin reductase activity at low, micromolar concentrations (IC$_{50}$ after 5 min was 13 μM). Amongst the others, only compound 3a slightly inhibited thioredoxin reductase activity, but at considerably higher concentrations than PX-12 (IC$_{50}$ nearly three times higher).

TABLE 2

| | IC$_{50}$ of thioredoxin reductase activity inhibition [μM] | | | |
|---|---|---|---|---|
| Measurement time, from reaction onset | PX-12 | 3a | 8a | 8b |
| 5 min | 13 | 37.1 | >40 | >40 |
| 15 min | 24 | >40 | >40 | >40 |

2.1.3. Evaluation of Glutathione Reductase Activity

The spatial structures of the active centres of glutathione reductase and the enzymes of the Trx-TrxR system show a high similarity. In order to further evaluate the selectivity of the evaluated compounds, their activity was evaluated against glutathione reductase in comparison to the known inhibitor PX-12. The reactions for determining the activity of recombinant human glutathione reductase made use of a chromogenic reaction with 5,5'-dithiobis-2-nitrobenzoic acid, like in the case of thioredoxin reductase. Activity was determined after 5 and 10 min incubation at room temperature. The reaction made use of reagents according to the Glutathione Reductase Assay Kit (Sigma) and human recombinant thioredoxin reductase (Sigma) at a concentration of 0.04 U. The only active compound among the evaluated group was PX-12, which inhibited glutathione reductase activity at micromolar concentrations (IC$_{50}$ after 5 min was 19.8 μM). None of the other evaluated compounds (3a, 8a and 8b) inhibited glutathione reductase activity, even at a concentration of 100 μM. The results shown in Tables 1, 2 and 3 indicate that compounds 3a, 8a and 8b are considerably more selective inhibitors of thioredoxin than PX-12.

TABLE 3

| IC$_{50}$ of glutathione reductase activity inhibition [μM] | | | | |
|---|---|---|---|---|
| Measurement time, from reaction onset | PX-12 | 3a | 8a | 8b |
| 5 min | 19.8 | >100 | >100 | >100 |
| 10 min | 28.6 | >100 | >100 | >100 |

2.2. Evaluation of the Cytostatic/Cytotoxic Activity of the Evaluated Compounds

The cytostatic/cytotoxic activity was evaluated using the following lines of tumour cells: EMT6 (murine breast cancer), PANC02 (murine pancreatic cancer), B78 (murine melanoma), C-26 (murine colon cancer), K562 (human chronic myelogenic leukaemia), T24 (human bladder cancer), RAJI (human Burkitt's lymphoma), Ramos (human Burkitt's lymphoma). The cultures were maintained in the following media: DMEM (EMT6, PANC02, B78), RPMI (C-26, Raji, Ramos), IMDM (K562), McCoy's (T24) with an addition of 10% bovine serum (Invitrogen) and antibiotics (Sigma).

To determine cytostatic/cytotoxic activity of the evaluated compounds, cell cultures were initiated in 96-well plates. After 24 h, inhibitors were added at set concentrations. The results were determined using colorimetric methods following 72 hours of incubation. To determine cytostatic/cytotoxic activity, crystal violet dyeing was used (reading at 595 nm) or MTT (Sigma; reading at 570 nm).

Table 4 compiles the results of the experiments (LD$_{50}$), in which the cytostatic/cytotoxic activity of the reference inhibitor thioredoxin PX-12 and compound 3a. In most of the evaluated lines of tumour cells, these compounds had a similar LD$_{50}$ value. Against line EMT6 (murine breast cancer) compound 3a turned out to be over two times more active.

TABLE 4

| LD$_{50}$ of the evaluated compound [μM] after 72 h of incubation | | |
|---|---|---|
| Tumour cell line | PX-12 | 3a |
| EMT6 | 12.7 | 5.3 |
| PANC02 | 3.8 | 3.2 |
| C-26 | 5.4 | 3.2 |
| B78 | 5.3 | 4.3 |
| RAJI | 5.9 | 4.6 |
| Ramos | 3.7 | 3.3 |
| K562 | 4.9 | 3.8 |
| T24 | 4.5 | 5.1 |

Similar analyses were performed for the other evaluated compounds. The results are shown in FIG. 1. All of the compounds exhibit cytostatic/cytotoxic activity against tumour cells, strongest against cells derived from the hematopoietic system (chronic myelogenic leukaemia K562, Burkitt's lymphoma RAJI).

2.3. Analysis of the Cell Cycle—Effect of the Evaluated Compound on Cell Division The cell cycle is composed of a series of events leading to cell division. In the cell cycle we differentiate the following phases: G1 (interval between divisions), S (duplication of genetic material) and G2/M (division or mitosis). An analysis of the cel cycle using a flow-through cytometer makes it possible to determine the percentage of cells in each of the phases. Furthermore, the percentage of cells in the so-called subG1 phase: those, whose genetic material has degraded as a result of apoptosis or necrosis.

The cell cycle was examined using the cancer line T24 following 72 hours of incubation with PX-12 and a racemic mixture of 3a. The cells were stained with propidium iodide at 10 μg/μl and analysed with flow-through cytometry. The results of this analysis are shown in FIG. 2. The percentage of dividing cells duplicating their genetic material (S phase) is clearly lower after incubation with inhibitors of thioredoxin.

BIBLIOGRAPHY

Berggren, M., Gallegos, A., Gasdaska, J. R., Gasdaska, P. Y., Warneke, J., Powis, G., *Anticancer Res* 1996, 16, pp. 3459-3466
Gromer S., Urig S., Becker K. *Med. Res. Rev.* 2004 24, 1, pp. 40-89
May J. M., Mendiratta S, Hill K. E., Burk R. F., *J. Biol. Chem.*, 1997; 272, pp. 22607-22610
Holmgren, A., J. Biol. Chem. 1989, 264, pp. 13963-13966
Ichijo, H., Nishida, E., Irie, K., ten Dijke, P., *Science* 1997, 275, pp. 90-94
Sasada, T., Nakamura, H., Ueda, S., Sato, N., *Free Radic. Biol. Med.* 1999, 27, pp. 504-514
Kirkpatrick, D. L., Kuperus, M., Dowdeswell, M., Potier, N., *Biochem. Pharmacol.* 1998, 55, pp. 987-994
Calabrese, V., Bates, B. E., Mancuso, C., Cornelius, C., Ventimiglia, B., Cambria, M. T., Di Renzo, L., De Lorenzo, A., Dinkova-Kostova D., *Mol. Nutr. Food Res.* 2008, 52, pp. 1062-1073
Fang, J., Lu, J., Holmgren, A., *J. Biol. Chem.* 2005, 280. pp. 25284-25290
Sun, Q., Wu, Y., Zappacosta, F., Jeang, K. T., Lee, B. J., Hetfield, L. D., Gladyshev, N. V., *J. Biol. Chem.* 1999, 274, pp. 24522-24530
Nordberg, J., Zhong, L., Holmgren, A., Amer, E. S., *J. Biol. Chem.* 1998, 273, pp. 10835-10842
Gromer, S., Arscott, L. D., Williams, C. H., Jr., Schirmer, R. H., Becker, K., *J. Biol. Chem.* 1998, 273, pp. 20096-20101
Marzano, C., Gandin, V., Folda, A., Scutari, G., *Free Radic. Biol. Med.* 2007, 42, pp. 872-881

What is claimed is:

1. A compound with the general formula (I): . . . R3 is a trifluoromethyl or 2,6-di(trifluoromethyl)benzoyl or a benzoyl having at positions 2,6 two identical or different halide substituents selected from the group consisting of Cl, Br, I or a pharmaceutically acceptable salt thereof.

2. The compound according to claim 1, wherein:
   R1 is a linear or branched C1-C8 alkyl group, substituted or not substituted phenyl group, or a benzyl group;
   R2 is a hydrogen atom, or a CONHCH2COOX group, wherein X is a linear or branched C1-C6 aliphatic substituent; and
   R3 is trifluoromethyl a 2,6-dichlorobenzoyl or 2,6-di(trifluoromethyl)benzoyl.

3. The compound according to claim 1, selected from the group consisting of:
   (R)-2-((1-((2-ethoxy-2-oxoethyl)amino)-4-methyl-1-oxopentan-2-yl)carbamoyl)allyl 2,6-bis(trifluoromethyl)benzoate;
   (S)-2-((1-((2-ethoxy-2-oxoethyl)amino)-4-methyl-1-oxopentan-2-yl)carbamoilo)allyl 2,6-bis(trifluoromethyl)benzoate;

2-((1-((2-ethoxy-2-oxoethyl)amino)-4-methyl-1-oxopentan-2-yl)carbamoyl)allyl 2,6-bis(trifluoromethyl)benzoate;

2-((1-((2-ethoxy-2-oxoethyl)amino)-4-methyl-1-oxopentan-2-yl)carbamoyl)allyl 2,6-dichlorobenzoate;

2-(benzylcarbamoyl)allyl 2,6-bis(trifluoromethyl)benzoate; and 2-(benzylcarbamoyl)allyl 2,6-dichlorobenzoate.

4. The compound of claim 1, wherein R1 is —CH$_2$CH(CH$_3$)$_2$; R2 is —CONH$_2$CH$_2$COOEt; and R3 is 2,6-Cl$_2$—PhCO—.

5. A pharmaceutical composition comprising an effective amount of an active ingredient having the general formula (1), according to claim 1 and a pharmaceutically acceptable carrier.

6. The composition of claim 5, wherein the active ingredient of the R1, R2, and R3 substituents of formula (1) are respectively —CH$_2$CH(CH$_3$)$_2$; —CONH$_2$CH$_2$COOEt; and 2,6-Cl$_2$—PhCO—.

7. A method for treatment of a condition selected from the group consisting of breast cancer, pancreatic cancer, colon cancer, bladder cancer, melanoma, chronic myelogenic leukemia, or Burkitt's lymphoma comprising administering to a subject in need thereof an effective amount of a compound having the general formula (1), as defined in claim 1.

8. A method of treatment for a condition selected from the group consisting of breast cancer, pancreatic cancer, colon cancer, bladder cancer, melanoma, chronic myelogenic leukemia, or Burkitt's lymphoma, comprising administering to a subject in need thereof an effective amount of the pharmaceutical composition according to claim 5.

* * * * *